(12) United States Patent
Li et al.

(10) Patent No.: US 9,116,145 B2
(45) Date of Patent: Aug. 25, 2015

(54) FLEXIBLE IC/MICROFLUIDIC INTEGRATION AND PACKAGING

(71) Applicant: The George Washington University, Washington, DC (US)

(72) Inventors: Zhenyu Li, Mcclean, VA (US); Mona E. Zaghloul, Bethesda, MD (US); Bowei Zhang, Arlington, VA (US); Can E. Korman, McLean, VA (US)

(73) Assignee: The George Washington University, Washington, DC (US)

( * ) Notice: Subject to any disclaimer, the term of this patent is extended or adjusted under 35 U.S.C. 154(b) by 0 days.

(21) Appl. No.: 13/715,110

(22) Filed: Dec. 14, 2012

(65) Prior Publication Data

US 2013/0243655 A1 Sep. 19, 2013

Related U.S. Application Data

(60) Provisional application No. 61/570,627, filed on Dec. 14, 2011.

(51) Int. Cl.
| | |
|---|---|
| H01K 3/00 | (2006.01) |
| H01R 43/00 | (2006.01) |
| H01L 21/50 | (2006.01) |
| H05K 3/00 | (2006.01) |
| B01L 3/00 | (2006.01) |
| G01N 33/00 | (2006.01) |
| G01N 33/50 | (2006.01) |
| H01L 23/498 | (2006.01) |
| B81C 1/00 | (2006.01) |

(Continued)

(52) U.S. Cl.
CPC .......... *G01N 33/50* (2013.01); *B01L 3/502707* (2013.01); *B01L 3/502715* (2013.01); *H05K 3/0014* (2013.01); *B01L 2200/12* (2013.01); *B01L 2300/0663* (2013.01); *B01L 2300/0816* (2013.01); *B01L 2300/0848* (2013.01); *B81C 1/0023* (2013.01); *G01N 33/49* (2013.01); *H01L 23/49822* (2013.01); *H01L 2224/12105* (2013.01); *H05K 3/4038* (2013.01); *Y10T 29/49155* (2015.01)

(58) Field of Classification Search
USPC ......................................... 422/68.1, 502–507
See application file for complete search history.

(56) References Cited

U.S. PATENT DOCUMENTS

| | | | |
|---|---|---|---|
| 6,294,831 B1 * | 9/2001 | Shishido et al. | 257/729 |
| 6,548,895 B1 * | 4/2003 | Benavides et al. | 257/712 |

(Continued)

OTHER PUBLICATIONS

Christen et al, "Design, Fabrication, and Testing of a Hybrid CMOS/PDMS Microsystem for Cell Culture and Incubation," IEEE Transactions on Biomedical Circuits and Systems, vol. 1, No. 1, Mar. 2007.*

T. Thorsen et al., "Microfluidic Large-Scale Integration," Science, vol. 298, 2002, pp. 580-584.

S. Cheng et al., "Liquid Metal Stretchable Unbalanced Loop Antenna," Applied Physics Letters 94, 144103, American Institute of Physics, 2009, 3 pages.

(Continued)

*Primary Examiner* — Jennifer Wecker
(74) *Attorney, Agent, or Firm* — Blank Rome LLP

(57) ABSTRACT

A flexible IC/microfluidic hybrid integration and packaging method and resulting device. A single flexible elastomer substrate, such as polydimethylsiloxane (PDMS), has dedicated microchannels filled with liquid metals (or low melting point solders) to provide electrical interconnects to a solid-state IC die, such as CMOS, and additional microchannels for hybrid integration with microfluidics without performing any post-processing on the IC die. The liquid metal used can be a gallium-indium-tin eutectic alloy (also called Galinstan).

25 Claims, 10 Drawing Sheets

Schematic illustration of the fabrication and packaging procedures to produce flexible IC/microfluidic hybrid microsystems. CMOS is used as an example IC technology.

(51) Int. Cl.
 *H05K 3/40* (2006.01)
 *G01N 33/49* (2006.01)

(56) References Cited

U.S. PATENT DOCUMENTS

| | | | | |
|---|---|---|---|---|
| 2006/0020371 | A1* | 1/2006 | Ham et al. | 700/266 |
| 2007/0109757 | A1* | 5/2007 | Lee et al. | 361/760 |
| 2007/0287191 | A1* | 12/2007 | Stiene et al. | 436/150 |
| 2008/0150154 | A1* | 6/2008 | Hedler et al. | 257/776 |
| 2008/0199362 | A1* | 8/2008 | Chong et al. | 422/100 |
| 2008/0199971 | A1* | 8/2008 | Tondra | 436/149 |
| 2009/0169427 | A1* | 7/2009 | Supriya et al. | 422/68.1 |
| 2009/0305901 | A1* | 12/2009 | Seemann et al. | 506/7 |
| 2010/0098585 | A1* | 4/2010 | Chiu et al. | 422/68.1 |
| 2010/0216282 | A1* | 8/2010 | Wang et al. | 438/118 |
| 2011/0045577 | A1* | 2/2011 | Bruzewicz et al. | 435/287.1 |
| 2012/0119360 | A1* | 5/2012 | Kim et al. | 257/737 |
| 2013/0193003 | A1* | 8/2013 | Reed et al. | 205/775 |

OTHER PUBLICATIONS

J. Cooper et al., "Poly(dimethylsiloxane) as a Material for Fabricating Micofluidic Devices," Accounts of Chemical Research, vol. 35, No. 7, 2002, pp. 491-499.

Marc A. unger et al., "Monolithic Microfabricated Valves and Pumps by Multilayer Soft Lithography," Science, vol. 288, No. 113, Apr. 7, 2000, pp. 113-116.

A. C. Siegel et al., "Cofabrication of Electromagnets and Microfluidic Systems in Poly(dimethylsiloxane)," Angew. Chem. Int. Ed., vol. 45, 2006, pp. 6877-6882.

Y. Xia et al. "Soft Lithography," Annu. Rev. Mater. Sci., 1998, vol. 28, pp. 153-184.

Z. Li et al., "Optofluidic Grating Spectrograph on a Chip," IEEE, 2009, 2 pages.

* cited by examiner

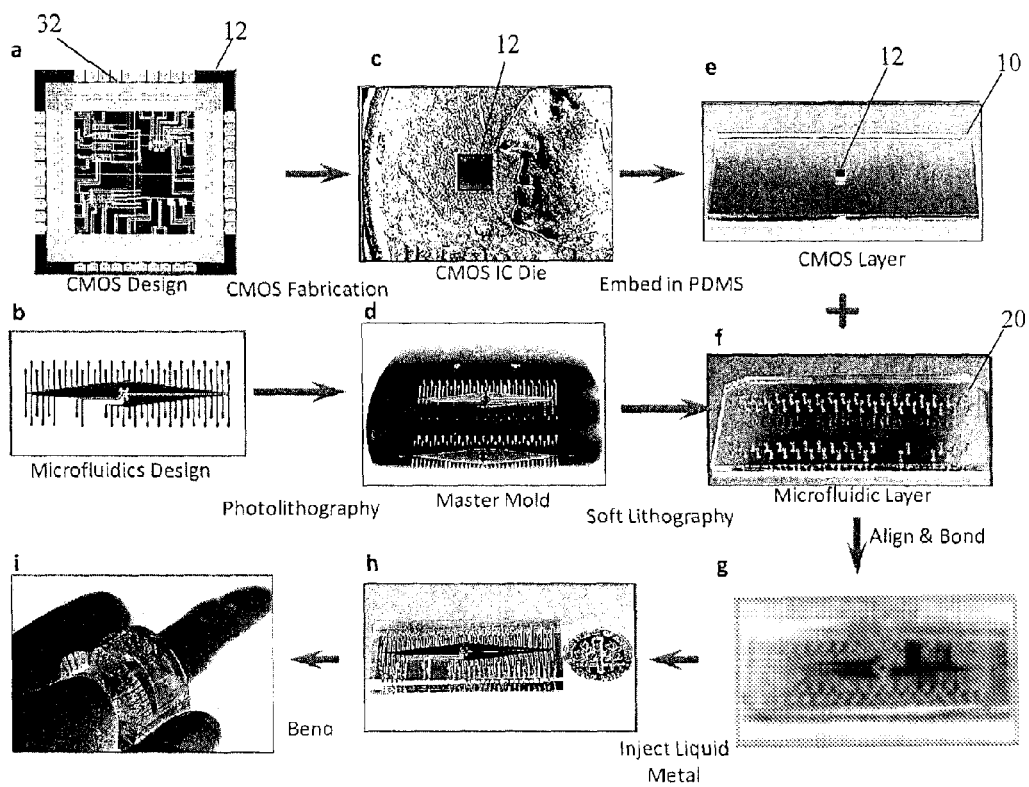
Figure 1. Schematic illustration of the fabrication and packaging procedures to produce flexible IC/microfluidic hybrid microsystems. CMOS is used as an example IC technology.

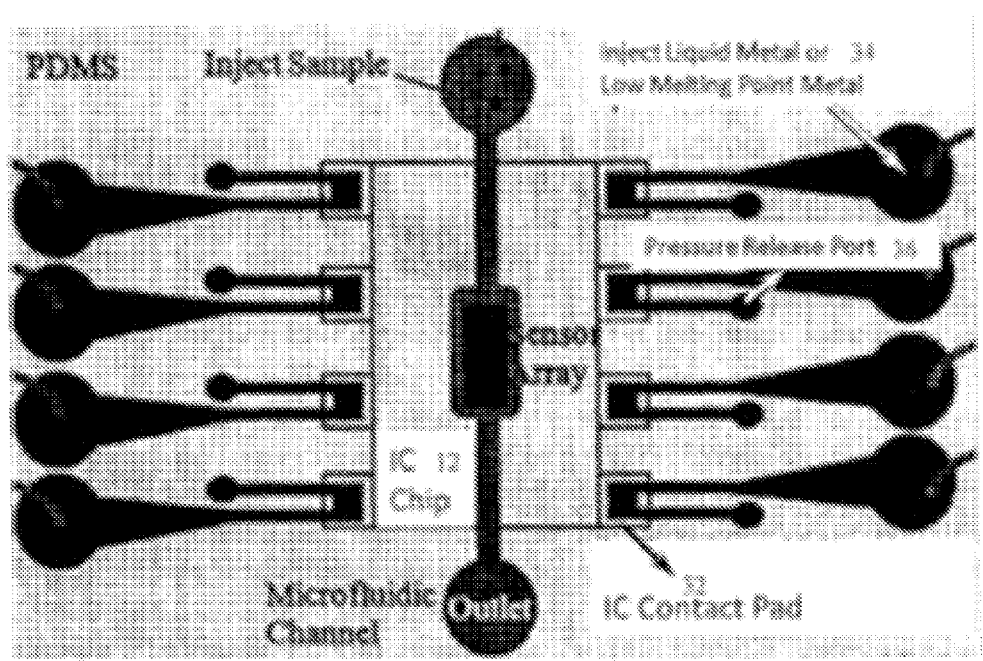
Figure 2, Schematic showing the liquid metal interconnects and a microfluidic channel integrated and packaged with an IC die in a flexible PDMS package.

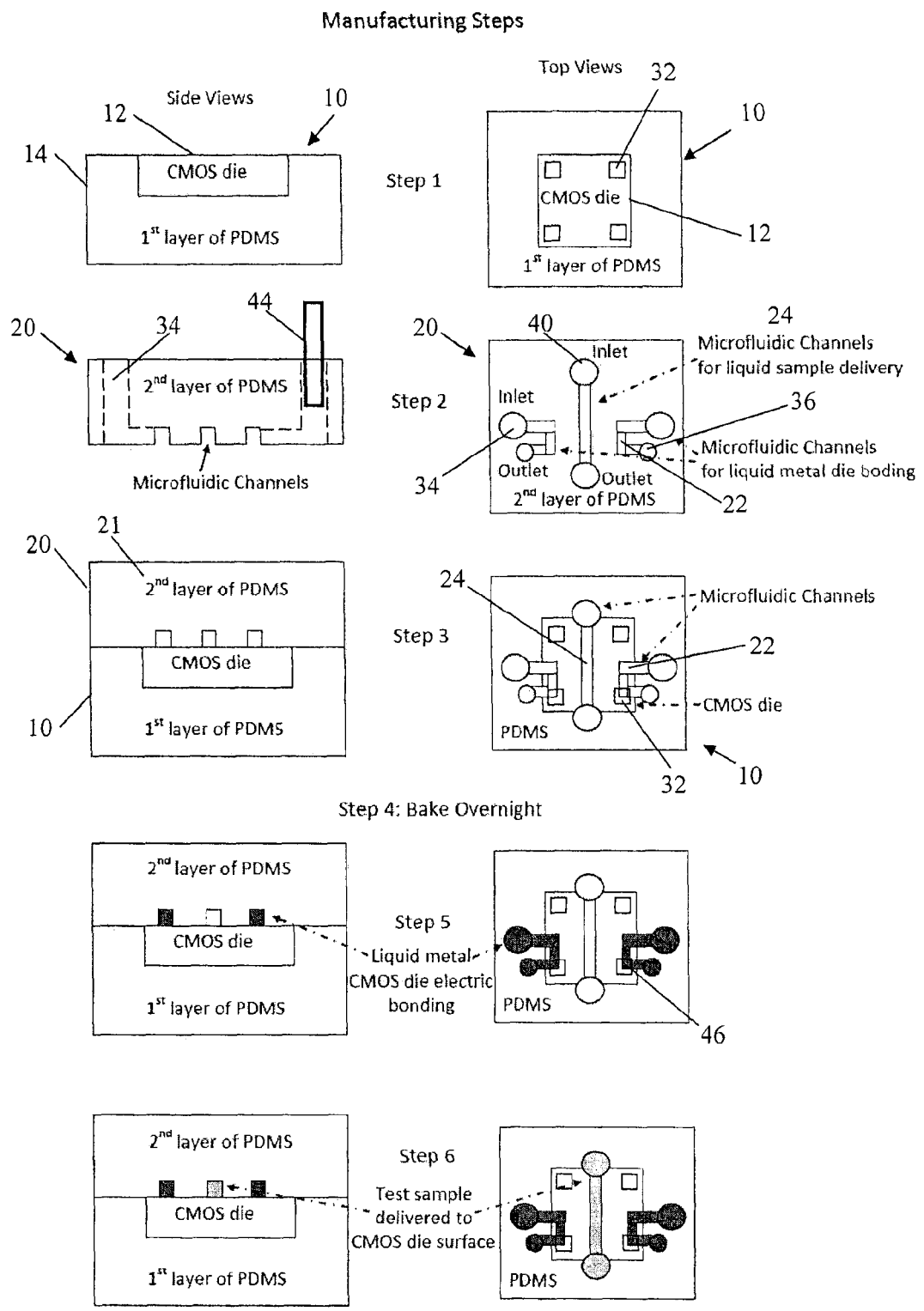
Figure 3, Manufacture Flow

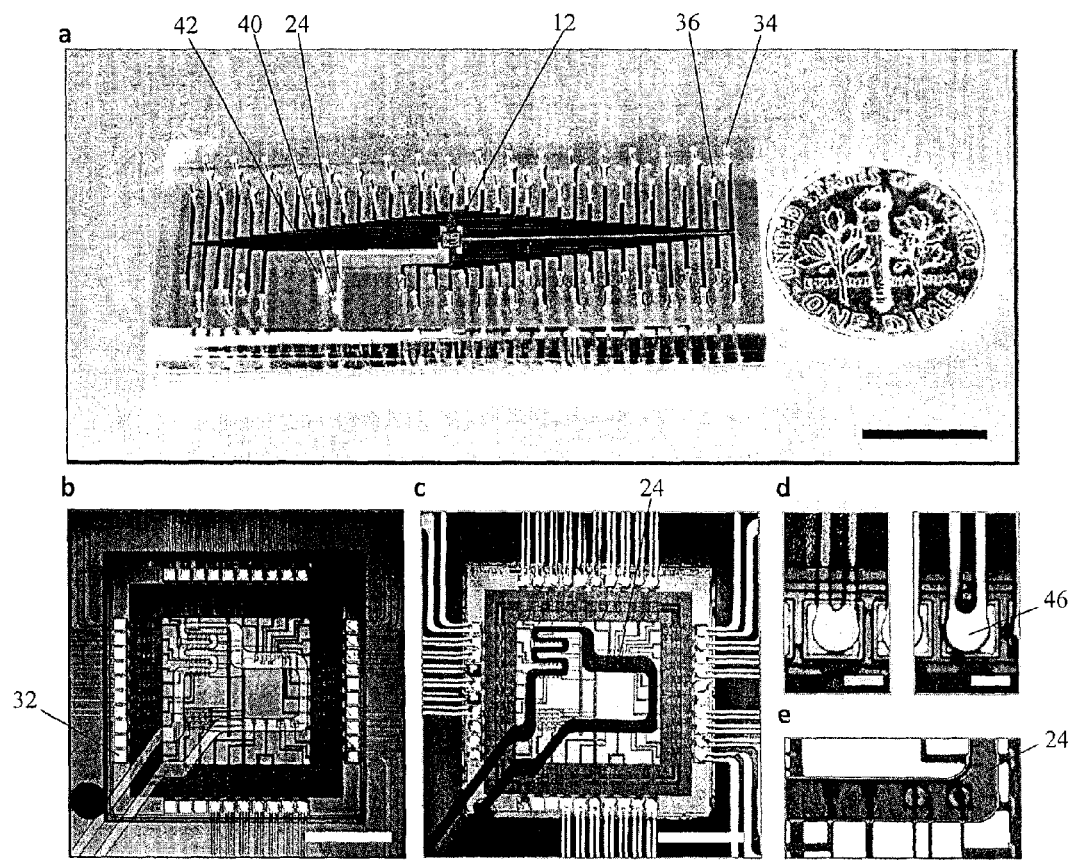
Figure 4. Liquid metal interconnects and microfluidic sample delivery in the packaged CMOS/microfluidic hybrid microsystem.

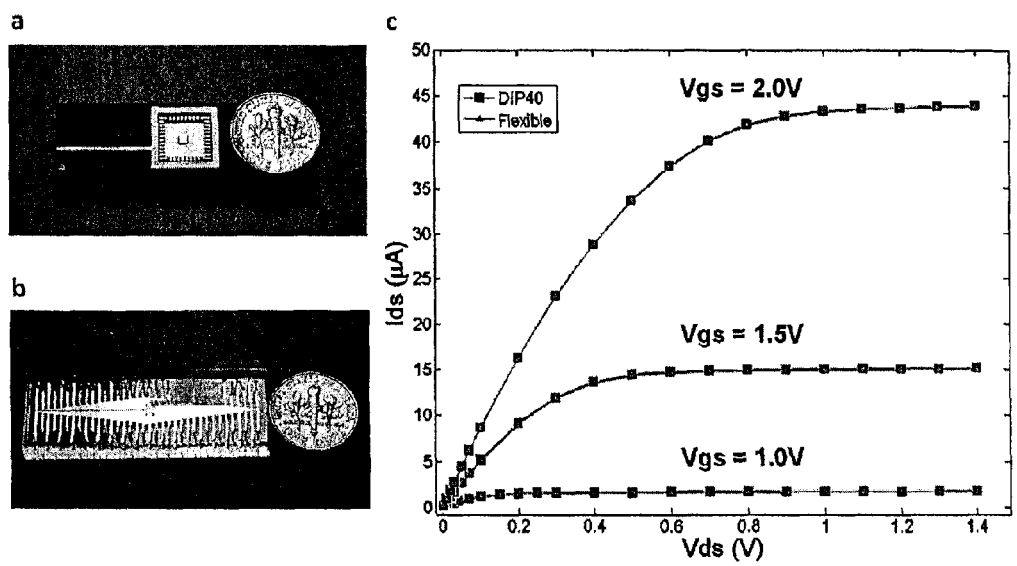
Figure 5. Measured Ids-Vds characteristics of NMOS transistors in conventional DIP and flexible packages

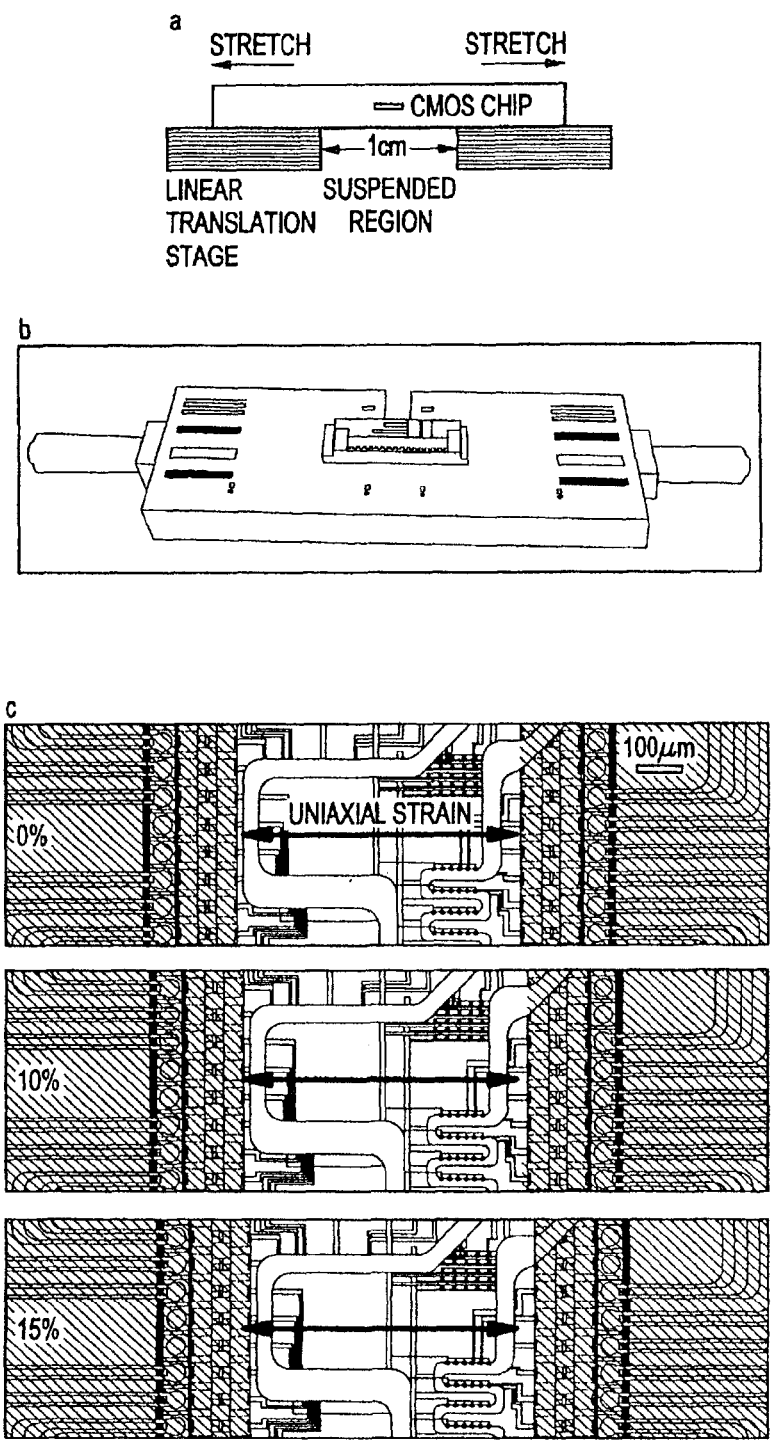
Figure 6. Measured I-V characteristics of an NMOS transistor in the flexible packages under different uniaxial stretching conditions.

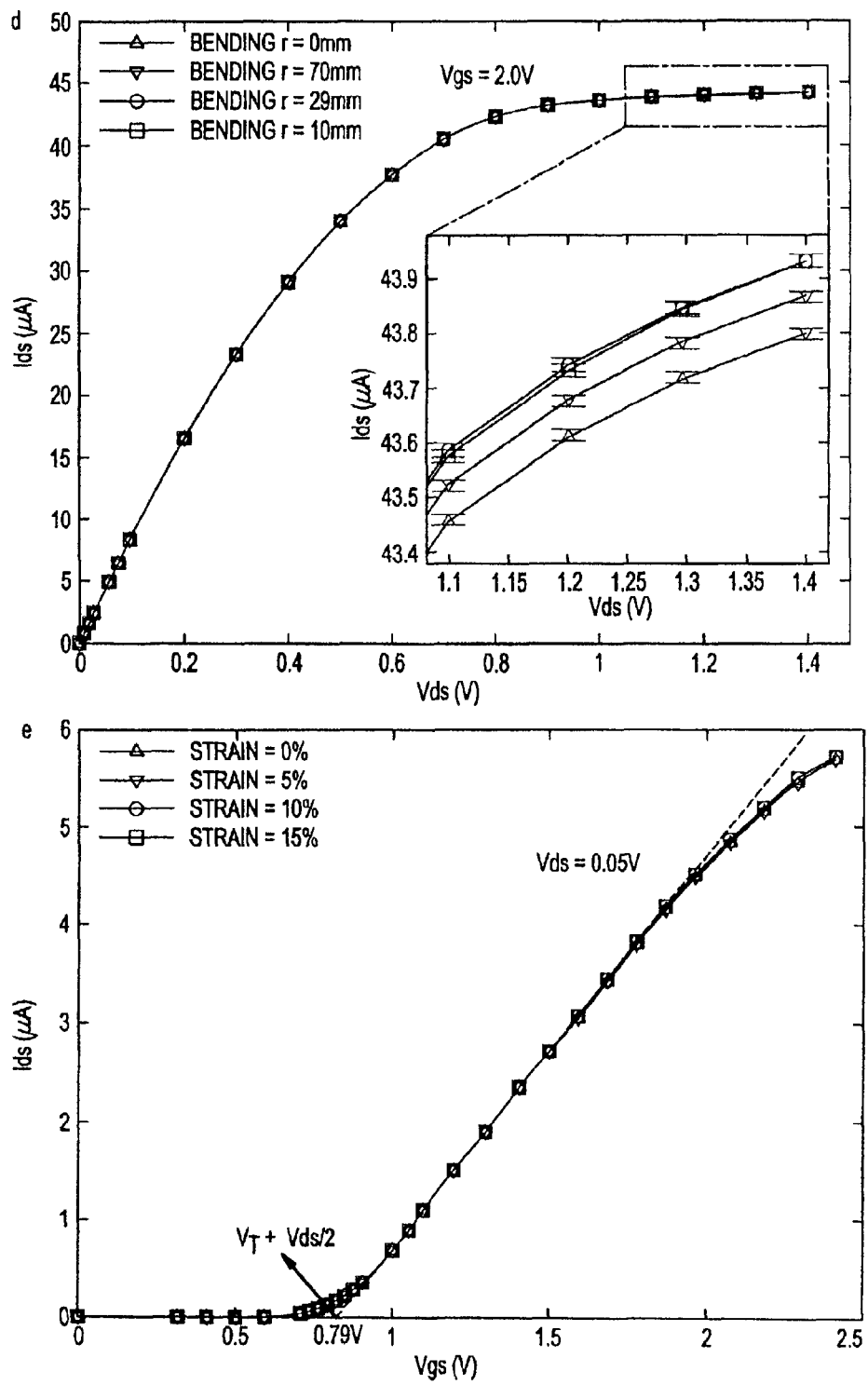
Figure 6. Measured I-V characteristics of an NMOS transistor in the flexible packages under unisxial stretching conditions.

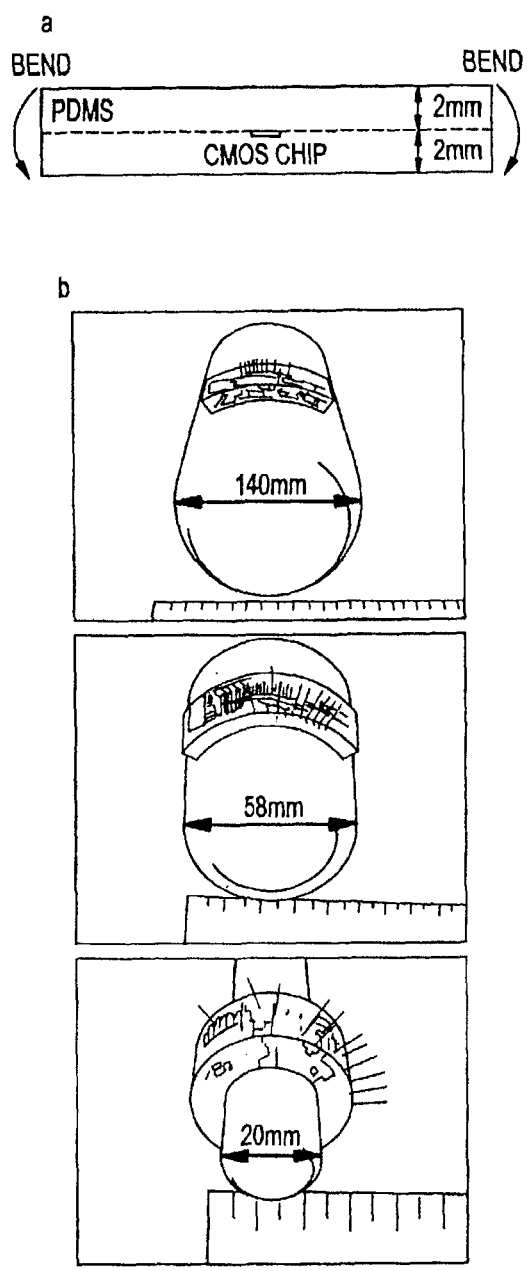
Figure 7. Measured I-V characteristics of an NMOS transistor in the flexible packages under different bending conditions.

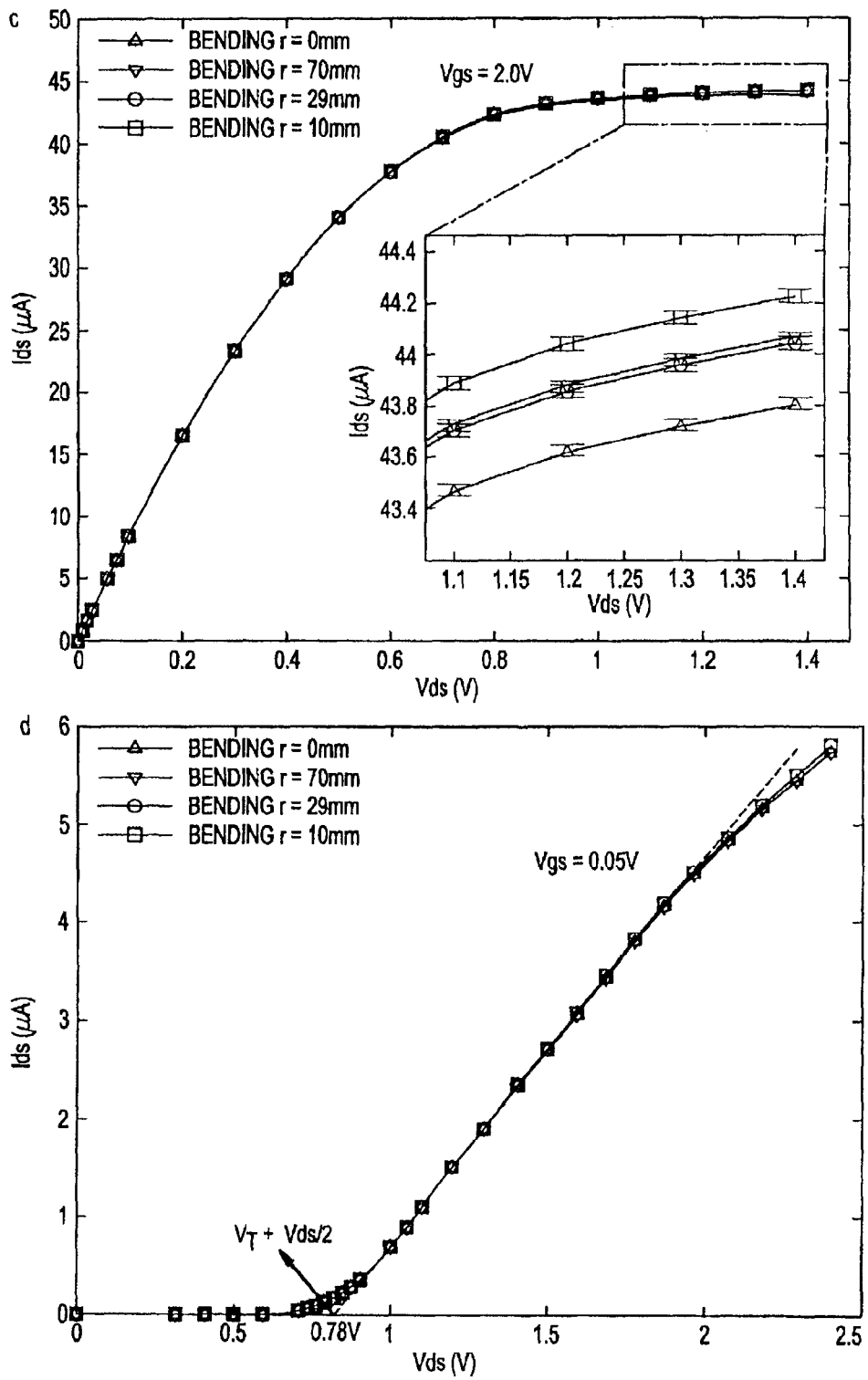
Figure 7. Measured I-V characteristics of an NMOS transistor in the flexible packages under different bending conditions.

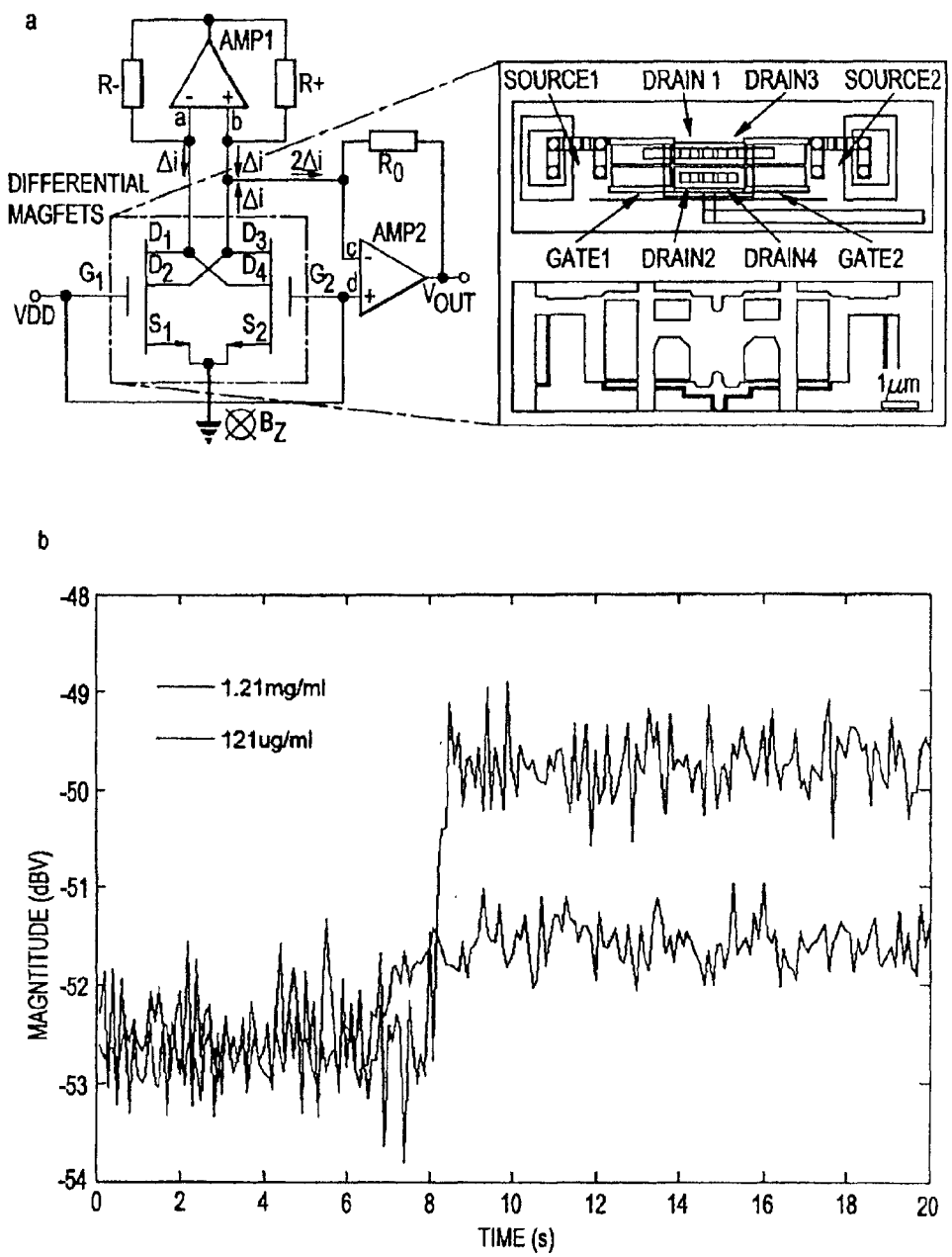
Figure 8. Detection of magnetic nanoparticles in water with a packaged CMOS MAGFET/microfluidic hybrid microsystem.

FLEXIBLE IC/MICROFLUIDIC INTEGRATION AND PACKAGING

RELATED APPLICATION

This application claims the benefit of U.S. Provisional Application No. 61/570,627, filed Dec. 14, 2011, the entire contents of which are incorporated herein by reference.

BACKGROUND OF THE INVENTION

Field of the Invention

The invention relates to integrated circuits (ICs) packaging, flexible electronics, sensors and microfluidics, and more particularly to a flexible IC/microfluidic hybrid microsystem for flexible electronics, sensing, wearable health monitoring and point-of-care medical diagnostics applications.

Flexible electronics enables unconventional placements of electronics, sensors and actuators and wireless communication components in conformal contact with nonflat surfaces, which are not achievable with rigid solid-state integrated circuit (IC) technology such as traditional complementary metal oxide semiconductor (CMOS) technology. However, current state-of-the-art flexible electronic systems have not yet matched the high performance, low power consumption, low cost and scalability offered by traditional IC technology. In addition, current flexible electronic systems rely on either organic molecules which often have low charge-carrier mobilities, or ultrathin inorganic semiconductor membranes which require delicate fabrication processes. On the other hand, typical IC die (or chip) measures in dimensions of only a few millimeters to a few centimeters square, easily attachable to common nonflat surfaces such as human bodies and aircraft surfaces with typical radii of curvature ranging from centimeters to meters. Therefore, a packaging technology capable of integrating IC components onto a flexible and biocompatible substrate will greatly enhance the performance of flexible electronic systems.

Another noticeable constraint on current flexible electronic systems is that they often provide only electronic and optoelectronic functionalities with little or no fluidic functions. A consequence of this constraint is that current flexible bioelectronic systems can measure only limited physical parameters such as temperature, pressure and biopotentials, but not biomolecular markers in bodily fluids which are extremely important for early disease diagnosis and treatment monitoring. A flexible technology allowing hybrid integration of solid state IC electronics/sensors with microfluidics can have transformative impacts on flexible bioelectronic systems by enabling previously unavailable biosensing capabilities such as continuous molecular biomarker monitoring embedded in a wearable device.

A key challenge in the flexible integration of solid state IC and microfluidics is that complex post-processing and packaging steps are often required, and the fabrication techniques involved are generally not compatible with flexible substrates. In particular, the commonly used wire bonding structure in solid state IC packaging is intrinsically a three dimensional (3D) structure, which makes it extremely difficult to integrate separate microfluidic devices on top. Other packaging techniques, such as flip-chip bonding, can result in flat device surfaces, however the active surface is buried within the package and not accessible for microfluidic integration.

SUMMARY OF THE INVENTION

This invention describes a novel flexible IC/microfluidic hybrid integration and packaging method and resulting device. In one example, we show a single flexible elastomer substrate, such as polydimethylsiloxane (PDMS), with dedicated microchannels filled with liquid metals (or low melting point solders) to provide electrical interconnects to a CMOS IC chip and additional microchannels for hybrid integration with microfluidics without performing any post-processing on the CMOS die. The liquid metal used can be a gallium-indium-tin eutectic alloy (also called Galinstan) that contains 68.5% gallium, 21.5% indium, and 10% tin, and melts at room temperature, or any other low melting metal materials which can be filled into microfluidic channels. Compared with mercury, Galinstan is nontoxic, nonevaporative, and has a higher electrical conductivity and better wetting properties. Similar gallium alloys have been used to fabricate on-chip coils, antennas and electrical wires for magnetic, RF and display applications. However, the invention can use any suitable liquid metal, such as those discussed in Siegel, A. C., Shevkoplyas, S. S., Weibel, D. B., Bruzewicz, D. A., Martinez, A. W. & Whitesides, G. M. *Cofabrication of electromagnets and microfluidic systems in poly(dimethylsiloxane)*, Angew. Chem. Int. Ed. 45, 6877-6882 (2006), and Cheng, S., Rydberg, A., Hjort, K., & Wu, Z. *Liquid metal stretchable unbalanced loop antenna*, Appl. Phys. Lett. 94, 144103 (2009). Those documents are hereby incorporated by reference.

Along with liquid metal interconnects, microfluidic components are co-fabricated on the same elastomer substrate aligned with the IC die, allowing seamless IC/microfluidic integration and flexible packaging. Besides flexible electronics and sensing applications, we believe this technology will also prove an enabling method in the fields of CMOS hybrid microsystems, MEMS, optoelectronics, RF electronics, lab-on-a-chip, implantable medical devices, optoelectronics and optofluidics by providing novel functions previously difficult, if not impossible, to integrate such as heat management, magnetic coils, tunable antennas, and metallic optofluidic components, particularly in a flexible form factor.

BRIEF DESCRIPTION OF THE FIGURES

FIG. 1 is a schematic illustration of the fabrication and packaging procedures to produce flexible IC/microfluidic hybrid microsystems. CMOS IC is used as an example IC technology.

FIG. 2 is a schematic drawing showing the liquid metal interconnects and a microfluidic channel integrated and packaged with an IC die in a flexible PDMS package.

FIG. 3 is manufacture flow of the flexible IC/Microfluidic systems.

FIG. 4(a) is an optical image of the packaged CMOS/microfluidic integrated system.

FIG. 4(b) is an optical micrograph showing the microfluidic channels are aligned with CMOS pads and sensors.

FIG. 4(c) is an optical micrograph showing the interconnect channels filled with liquid metal and the microfluidic sample delivery channel filled with sample solution.

FIG. 4(d) is an optical micrograph of an interconnect channel aligned with an IC contact pad before (left) and after (right) liquid metal is injected.

FIG. 4(e) is a view showing the microfluidic channel accurately aligned with the sensor area.

FIG. 5(a) is a view of the IC chip in a conventional DIP-40 package.

FIG. 5(b) is a view of the IC chip in a flexible PDMS package with liquid metal interconnects.

FIG. 5(c) is a graph of measured I-V curves of the NMOS transistors in the two different packages showing excellent agreements between each other.

FIG. 6(a) is a schematic showing the measurement setup. The central suspended region of the package is 1 cm long.

FIG. 6(b): is a photograph of the real setup showing the package glued to two linear translation stages.

FIG. 6(c) shows optical micrographs of the CMOS chip in the package under different uniaxial strains. It can be seen that most of the strain was in the PDMS/Liquid metal region.

FIG. 6(d) is a graph of measured $I_{ds}$-$V_{as}$ curves of the NMOS transistor under different linear strains showing excellent agreements among each other.

FIG. 6(e) is a graph of measured $I_{ds}$-$V_g$, curves of the NMOS transistor under different linear strains.

FIG. 7(a) is a schematic showing the measurement geometry. The CMOS chip is located near the neutral mechanical plane.

FIG. 7(b) is photographs showing the flexible package was conformally attached to cylindrical tubes with diameters from 140 mm to 20 mm.

FIG. 7(c) is a graph of measured $I_{ds}$-$V_{ds}$ curves of the NMOS transistor under different bending radii.

FIG. 7(d) is a graph of measured $I_{ds}$-$V_{gs}$ curves of the NMOS transistor under different bending radii.

FIG. 8(a) is an example readout circuit for the flexible IC/Microfluidic sensing system. Inset shows the design layout and optical micrograph of the IC sensor, which is a magnetic field effect transistor (MAGFET). Scale bar: 1 um.

FIG. 8(b) is a graph of system response to magnetite nanoparticles in water flowing above the sensor area.

DETAILED DESCRIPTION OF THE PREFERRED EMBODIMENTS

In describing the preferred embodiments of the present invention illustrated in the drawings, specific terminology is resorted to for the sake of clarity. However, the present invention is not intended to be limited to the specific terms so selected, and it is to be understood that each specific term includes all technical equivalents that operate in a similar manner to accomplish a similar purpose.

Turning to the drawings, FIGS. 1 and 3 illustrate the fabrication and packaging procedures to produce flexible IC/microfluidic hybrid microsystems. FIG. 3 depicts the manufacturing steps of the CMOS/microfluidic hybrid integration and packaging system. CMOS is used as an example IC technology. One possible packaging material, polydimethylsiloxane (PDMS), is a soft elastomer widely used in medical implants, industrial packaging, microfluidics, flexible electronics and micro-optics due to its low cost, easy fabrication, flexibility, biocompatibility and optical transparency. Other flexible polymer or elastomer materials can also be used for packaging.

The final packaged system is composed of two PDMS layers: a bottom CMOS layer 10 and a top microfluidic layer 20, though the bottom and top can be reversed. The process begins with the CMOS and the corresponding microfluidics layout design (FIGS. 1a, 1b). The CMOS layer 10 is fabricated as follows: at step 1 of FIG. 3, the bare CMOS die 12 (FIG. 1b) from the commercial foundry is placed upside down (i.e., with its front side down) on a flat silicon wafer. A small pressure (~5 Psi) is applied to the back side of the CMOS die 12 to hold the front side of the CMOS die 12 in contact with the wafer. A previously degassed PDMS prepolymer is poured onto the CMOS die 12 and baked at 80° C. for 30 minutes. The CMOS layer 10 is then peeled off from the silicon wafer and the CMOS die 12 is now embedded in this piece of flat PDMS (CMOS layer 10) with its active surface still exposed. The final assembly is shown in FIG. 1e and FIG. 3, at step 1. The CMOS design fabrication process of the invention can be performed, for instance, by a commercial CMOS foundry.

Still referring to FIGS. 1 and 3, the PDMS microfluidic layer 20 is fabricated using conventional soft lithography techniques. First a patterned photo-resist master mold (FIG. 1d; e.g., SU8) is fabricated on a silicon wafer using photolithography. Then PDMS prepolymer is poured onto the mold and degassed in a vacuum chamber. The prepolymer is then baked at 80° C. for 30 minutes. The partially cured PDMS is peeled off from the mold forming the microfluidic layer 20 (FIG. 1f and FIG. 3, step 2), and the liquid inlet/outlet ports 34, 36 are punched through the whole microfluidic layer (FIG. 4). Later this microfluidic layer is bonded with the other PDMS layer (CMOS layer 10) embedded with the CMOS die to form the complete package and the through holes are sealed. The finished microfluidic layer 20 is shown in FIG. 3, step 2. Here, the microfluidic layer 20 includes a body 21 that has various microfluidic channels 22, 24.

The microfluidic layout design is used to generate a photomask through either a commercial photomask vendor or an in-house direct laser writer or a 3D printer. The microfluidic layout design determines the microfluidic channel dimensions and their locations in the package. The invention can utilize any conventional soft lithography technique, such as discussed in Xia, Y. N. & Whitesides, G. M. Soft lithography. *Annu. Rev. Mater. Sci.* 28, 153-184 (1998), which is hereby incorporated by reference. In the embodiment shown, the layout design is a computer file, and it's used to generate a photomask. Then the photomask is used in the photolithography step to generate the master mold used in the soft lithography step. Finally, soft lithography is used to make the PDMS microfluidic (i.e. layer 20) devices.

For each different CMOS layout, a different mold (FIG. 1d) is needed to fabricate the corresponding microfluidic layer 20 (FIG. 1f). However, the finished master molds can be reused many times, thus reducing the fabrication cost and time. Both the CMOS layer 10 (FIG. 1e) and the microfluidic layer 20 (FIG. 1f) are treated with oxygen or air plasma in order to form a strong bond between the two layers. Then the microfluidic layer 20 is aligned on top of the CMOS layer 10 to form a permanent bond, (FIG. 3, step 3). The oxygen plasma increases the silanol groups (OH) at the surface of the PDMS layers 14, 21 which when brought together forms permanent covalent siloxane bonds (Si—O—Si). Afterward, the package is baked at 80° C. (FIG. 3, step 4) overnight (or for longer than 8 hours) to enhance the bonding strength (FIG. 3) and fully cure the PDMS, as shown in FIG. 1g.

The configuration of the various channels 22, 24 is best shown in FIG. 2. The IC chip 12 has a number of ports at its two opposing elongated sides, at which a respective IC contact pad 32 is located. An input port 34 is provided that is larger than the contact pads 32, to provide a larger connection point for connecting to the IC chip 12. The microfluidic channels 22 are formed between the contact pads 32 and the input ports 34. The channels 22 are wide at the contact pads 32 and taper inward toward the contact pads 32. The channels 22 are positioned above the contact pads 32 (which are in the first PDMS layer 10 and face the second PDMS layer 21) and overlap with the pads, so that when the channels 22 are filled with liquid metal, the liquid metal will make electrical contact with the pads 32.

After the layers 10, 20 are bonded to one another (FIG. 1g), the channels 22, 24 are surrounded on one side by the second PDMS layer 20 and on the other side by the first PDMS layer 10 and/or the CMOS die 12 so that the channels are completely enclosed, as best shown in the cross-sectional drawing of FIG. 3, step 3 (left side). The closed channels 22, 24 preferably have a square cross-section shape. Liquid metal, preferably Galinstan, is filled (FIG. 1h) into the closed microfluidic channels 22 to form electrical interconnects to the CMOS IC 12. The liquid is shown darkened in the two channels 22 for instance, in FIG. 3, steps 5-6. Liquid metal is used because of its mechanical flexibility, microfluidics compatibility and easy fabrication, and since it is electrically conductive to form an electrical connection with the pads 32. Liquid metal Galinstan maintains a liquid form between −19.5° C. and 1800° C. and has a viscosity of 0.0024 Pa·s (at 20° C.).

In order to inject liquid metal, each microfluidic channel 22 preferably has one inlet port 34 and one outlet port 36 for pressure release. The inlet port 34 and the outlet port 36 each extend upward (in the embodiment shown) through the second PDMS layer 21, as best shown by the dashed lines for the inlet port 34 in FIG. 3, step 2 (left side). Each channel 22 is continuous and extends from the input port 34 to the contact pad 32, forms a U-shape across the face of the contact pad 32, and extends back to the release port 36. The liquid metal is introduced through the input port 34, travels the entire length of the channel 22, and enters the outlet port 36. As the liquid metal travels through the channel 22, air in the channel is pushed into the outlet port 36, where it can escape via a tube (discussed below). The pads 32 are typically between 50 microns to a few hundred microns wide. The channels 22 can be, for instance, 4 microns wide and 2 microns tall. Larger or smaller channels can be utilized, but wider channels 22 are easier to fill (a 10-20 um wide and 2 cm long channel can take a few seconds) and require less pressure. Once the liquid metal is in place, the inlet and outlet ports 34, 36 can be sealed, such as by PDMS material placed into those openings in the second PDMS layer 21, to prevent any liquid metal from escaping.

The liquid metal forms direct electrical contact with the individual IC contact pads 32. Electrical contact can then be made with the respective input port 34, as shown by the lead lines in FIG. 2. The input port 34 is much larger than the contact pad 32, which makes it easier to connect to a lead line. The electrical signal is then carried between the contact pad 32 and the lead line via the conductive liquid metal.

It is important to avoid water moisture between the Galinstan and the aluminum CMOS pads 32 because water can react with the Aluminum pads 32 in the presence of Gallium to generate $Al(OH)_3$ and Hydrogen gas. The whole fabrication process doesn't involve harsh chemicals or high temperatures that might otherwise damage the CMOS device. It is noted that gallium can corrode the aluminum pads 32; however, the corrosion does not cause noticeable performance degradation. Gallium is well known to attack other metals such as Aluminum. However, the corrosion of Gallium on Aluminum is a purely physical effect (Aluminum dissolving in Gallium) and the two metals form an alloy, which doesn't affect the electrical conductivity significantly. Copper appears to be resistant to attack by Gallium at 100° C. In addition, Gallium does not attack Tungsten, a common Via material used in many IC fabrication (including CMOS) processes. Even after five weeks of contact with Galinstan and repeated testing under bending conditions (see FIG. 1i), the CMOS die we used remained fully functional. If for any application the Gallium corrosion is not acceptable, protection layers such as Tungsten can be deposited on the contact pads. Another concern is the quick oxidation of Gallium in air forming a thin Gallium Oxide layer which may introduce additional capacitance at the contact pads affecting the AC performance of the circuits. For low frequency modulations (10 kHz) signals we didn't observe any performance degradation.

The other microfluidic channels 24 (that are not filled with liquid metal) provide microfluidic functions such as liquid sample delivery/manipulation to the CMOS IC 12, for instance to deliver blood. External pressure, on-chip MEMS pumps or capillary actions can be used to drive sample liquids from input port 40 to the IC sensor area (e.g. electrochemical, magnetic, MEMS, optical etc.) guided by the microfluidic sample delivery channel 24. The sample liquid will exit from the outlet port 42. The inlet and outlet ports 40, 42 each extend upward through the second PDMS layer 21 (as with inlet port 34, shown in FIG. 3, step 2 (left side)). Thus, the sample (such as blood) can be introduced into the inlet port 40 through the PDMS layer 21, and into the sample channel 24. As the sample passes through the channel 24, it forces any air in the channel out through the outlet port 42. Excess sample may also exit through the outlet port 42. The inlet and outlet ports 40, 42 can optionally be sealed after use, such as by a plug or the like. As shown in FIG. 3, step 6, the blood enters the input port 40 and travels to the output port 42, as represented by the grey shadowing.

FIG. 4a is a photograph of the packaged CMOS and microfluidics integrated system. The thickness of the whole package can vary from 1.5 mm to 5 mm, depending on the amount of PDMS used. Thinner devices are more flexible. The footprint of the whole package is about 2 cm by 5 cm when using a 40 pad CMOS chip. This footprint is limited by the number of input/output (I/O) ports that are needed to inject liquid metals to make electrical connections. The size of each (I/O) port is about 750 um in diameter and must be separated from each other by about 1 mm. However, for applications such as wireless sensing where the power source and I/O components are fully integrated in the package, such I/O ports are not needed and the final package size can be much smaller. At the center of the packaged device, a CMOS die 12 of 1.5 mm by 1.5 mm in size is embedded.

As shown in FIG. 4b, microfluidic channels aligned with the contact pads on the CMOS die are filled with Galinstan to allow electrical connections to the CMOS circuits while a separate microchannel is used for liquid sample delivery to the sensor area. The Galinstan can be used to fabricate on-chip microphotonic components integrated with PDMS microfluidics. The Galinstan can also be injected into microchannels as small as 4 μm wide and 2 um high.

Stainless steel tubes 44 (FIGS. 7b and 3, step 2) can be plugged into the access ports 34, 36 to inject liquid metal into the channels 22. Tubes are also provided at the inlet and outlet ports 40 of the sample channel 24 to allow for the delivery of a sample at the inlet port and for air to escape through the outlet port 40. The holes are punched during the fabrication step f of FIG. 1. The tubes 44 can extend partially into the ports (as shown in FIG. 3), or fully to the bottom of the port. After the liquid metal is filled into the channels 22, the stainless steel tubes can be left in the holes to facilitate electrical connections to the test equipments. The tubes can be removed after the lead lines are positioned, then the access ports 34, 36 can be plugged or sealed to prevent liquid metal from escaping.

As shown in FIGS. 4(b), and 4(c), 32 microfluidic channels were accurately aligned with the corresponding CMOS pads 32. Each channel also has a venting port 36 to avoid high pressure buildup during liquid metal injection. The pad size in our CMOS chip design is 80 μm by 80 μm with 15 μm gap between pads. So the microfluidic channels 22 were designed with a 50 μm diameter contact area or tip 46 with the pads. The channels 22 connected with the tip are as narrow as 15 μm in width and 20 μm in height. As the channels 22 move away from the tip 46, the width of the channels is increased to larger values (50 μm and 100 μm) for smaller electrical resistance of the interconnection.

The measured resistivity of Galinstan is $(2.85+/-0.09) \times 10^{-7}$ Ω·m and the total resistance due to liquid metal is between 5Ω and 15Ω depending on the length of the channel. The alignment accuracy was +/−5 μm using manual alignment under a 180× magnification stereoscope. If needed, mask aligners can be used to achieve sub-micron alignment accuracy. FIG. 5*d* shows the liquid metal contacting a CMOS pad 32. An additional 70 μm wide microfluidic channel is aligned with the CMOS sensor area for accurate liquid sample delivery, as highlighted by the shaded (darkened) area 24 shown in FIGS. 4(*c*) and 4(*e*). Typical channel dimensions are 50-100 μm wide, 10 μm high, though other sizes can be utilized. Microfluidic sample delivery channels 24 can be designed to match the locations and sizes of the sensor area on the IC die so that small volume liquid samples can be precisely delivered to the sensor area with close proximity. As shown, for instance, in FIGS. 4*b* and 4*c*, the channel 24 can extend substantially about the surface of the IC die. The entire channel 24 can be in contact with the surface of the die and come into contact with any of the electrical contacts on the die that are not coated with insulation (FIG. 4*e*). As shown and described, the entire channel 24 is at the top surface of the second PDMS layer 21. However, portions of the channel can be at the top surface of the second PDMS layer 21, and other portions of the channel 24 can be below the top surface of the second PDMS layer 21. In that manner, not all of the liquid metal in the channel 24 comes into contact with the IC die.

The flexible IC/microfluidic integration and packaging technology described here enables the seamless integration of CMOS sensor chips with PDMS microfluidics, thus achieving a true lab-on-a-chip system that have both CMOS functionalities and microfluidic sample manipulation on the same flexible substrate. By integrating PDMS microfluidics with CMOS sensor chips, a number of additional advantages can be obtained compared with traditional biosensor devices where fluidics and sensor device are decoupled. For example, by using active fluidic flow and reducing the distances between target molecules and sensor surface, more efficient and faster molecular binding can be achieved, which can improve both the detection sensitivity and throughput.

In the case of CMOS optical sensors, by using a shallow channel, we can not only obtain high photon collection efficiency and reduced background, but also eliminate the complex and bulky optics used in conventional optical sensing configurations. In addition, by combining CMOS actuators/electronics with PDMS valves, fully integrated on-chip valves and pumps may become possible without relying on any external pressure sources. Such self-contained compact IC/microfluidic hybrid microsystems can find many applications in point-of-care diagnostics, environmental monitoring and food safety inspection applications. The flexible integration of solid state IC electronics, sensors and microfluidics also holds great potential for wearable wireless monitoring of human health where real-time and continuous health/wellbeing data can be obtained and wirelessly communicated to the doctor or a central database for accurate and timely interpretation.

First, the flexible packaging of IC electronics/sensors can enable flexible electronics, display, wireless communication systems, optoelectronics, MEMS and sensor systems which can be conformally attached to nonflat surfaces such as human skin, eye balls (contact lens electronics), glasses, internal organs, clothes, aircraft surfaces (say wings), industrial pipes and buildings etc. Second, the flexible packaging of IC electronics and sensors with microfluidics can result in portable and low cost in-vitro diagnostics and molecular detection device, such as hand held molecular diagnostic, wearable bodily fluid analysis systems (glucose, cardiac Trophonin I/T or other biomarkers in bodily fluids) environmental monitoring, food safety inspection and bioterrorism detection devices.

Compared to current IC packaging methods, this invention has the following unique features and advantages: 1. A completely novel low-cost IC/Microfluidic hybrid integration and packaging method. 2. This invention can enable flexible (e.g., wearable, attachable, stretchable, bendable and twistable) electronic, display, sensor and communication systems based on industry-proven technologies (such as CMOS and III/V semiconductor ICs) with previously unavailable high performance, low cost, low power consumption and scalability. It can be stretchable with strain from 0%-200%, and bendable to form conformal contacts with legs, arms, wrist and fingers. 3. This invention can enable liquid samples, such as blood and urine, to be delivered directly to the IC electronic/sensor devices, extremely close to the sensor active area (i.e., the area covered by the microfluidic sample delivery channel 24). 4. Because this method can make test sample very close to the detector (several microns or direct contact), it makes the system have very high signal collection efficiency, thus easier to reach high sensitivity. 5. PDMS (or other suitable polymers) and liquid metal (or low melting point solder) are low cost materials, so this package method is low cost. 6. The fabrication process of this package is not complex, and highly repeatable, so it is suitable for high volume industry production. 7. This package method can make the device portable and handheld.

Accordingly, the invention provides point-of-care diagnosis to handle real-life samples such as blood and urine. The CMOS biosensor is packaged so that the electronic components are protected from the sample liquid while the test sample is delivered directly to the biosensor surface. The test sample can be very close to the detector (several microns) or directly contact the detector, which has a very high signal collection efficiency and makes it easier to reach high sensitivity.

EXAMPLE 1

As a non-limiting illustration of this invention and to verify the liquid metal interconnection, the contact pads of an enhanced-mode NMOS transistor (channel width W=5 μm, channel length L=10 μm) on a CMOS chip were connected using liquid metals. The NMOS transistor was designed in a 0.5 μm CMOS technology and fabricated by the On Semiconductor C5N 0.5 μm CMOS process. Two COMS dies with identical design were packaged into traditional dual-in-line 40 (DIP-40) package (FIG. 5*a*) and PDMS flexible package (FIG. 5*b*). As shown in FIG. 5*c*, the drain current vs. drain-to-source voltage (Ids-Vds) curve of the transistor was successfully measured. The NMOS transistor was connected in a common source configuration and the gate voltage was set at fixed values (Vgs=1.0V, 1.5V and 2.0V). The drain voltage Vds was swept from 0.1V to 1.4V and the drain current Ids was recorded. For comparison, the Ids-Vds curve of another NMOS transistor was also measured with the same design parameters and from the same fabrication process but packaged in a traditional dual-in-line 40 (DIP-40) package. The measured drain currents of the liquid metal connected transistor differed less than 1% from those of the DLP-40 packaged transistor.

In order to verify the package flexibility we also tested the transistor I-V characteristics when the package is under different uniaxial stretching conditions. The package was glued to two high resolution linear translation stages with a 1 cm long suspended region in the middle as shown in FIGS. 6(a) and 6(b). FIG. 6(d) shows the measured Ids-Vds curve of the transistor and FIG. 6(e) shows the measured Ids-Vgs curve. For the Ids-Vgs measurements, the NMOS transistor was biased at a low drain voltage Vds=0.05V and the gate voltage Vgs was swept from 0V to 2.4V.

The transistor remained fully functional under uniaxial strains up to 15% over the 1 cm suspended region, and the measured drain currents differed less than 0.5% from those of the flat PDMS package. The linearly extrapolated threshold voltage $V_T$ was 0.765V which agrees reasonably well with the foundry provided data of 0.7V. The highly reproducible device performance is partially contributed by the fact that the Young's modulus of Silicon (~130 to 170 GPa depending on orientation relative to the crystal lattice) is five orders of magnitude higher than that of PDMS (~1.5 MPa for RTV 615). Therefore, as can be seen in FIG. 6c, most of the strain is in the PDMS (and liquid metal) region of the package and the mechanical stress on the CMOS chip is quite small which is beneficial for stable device performance under stretching conditions.

We also measured the transistor I-V characteristics when the package is under different bending conditions. FIG. 7(a) shows the schematic setup for testing the packaged transistor under bending conditions. The package was conformally attached to a cylindrical tube with a radius ranging from 70 mm to 10 mm as shown in FIG. 7(b). In the tested package, both the top and bottom PDMS layers are 2 mm thick and therefore the CMOS die is located near the neutral mechanical plane. As shown in FIGS. 7(c) and 7(d), the NMOS transistor remained fully functional under bending radius of 10 mm, and the measured drain currents differed less than 1.5% from those of the flat PDMS package. The smallest bending radius at which we have observed functional transistors is 7.5 mm. If higher mechanical flexibility is required for the CMOS die, chemical mechanical polishing (CMP) can be used to thin the die from the current 250 μm to below 50 μm.

Most state-of-the-art CMOS/microfluidic hybrid systems (such as Lee, H. et al. *IC/microfluidic hybrid system for magnetic manipulation of biological cells*, IEEE J. Solid-State Circuits 41, 1471-1480 (2006), and Baltes, H. et al. (ed.) CMOS-MEMS: *Advanced Micro and Nanosystems* (Wiley-VCH, 2005), which are hereby incorporated by reference) rely on complex post-processing on the CMOS die or use only simple microfluidic reservoirs. As a demonstration of the proposed packaging technology, we integrated a CMOS magnetic sensor chip with a PDMS microfluidic sample delivery channel without performing any post-processing on the CMOS die. The CMOS magnetic sensor is a split-drain Hall effect magnetic field-effect transistor (MAGFET). When a MAGFET is exposed to a magnetic field, current deflection will produce an imbalance of the two drain currents due to the Hall effect. In our experiments, a differential MAGFET design was used to further improve the sensitivity. The MAGFET was designed in a 0.5 μm CMOS technology and fabricated by the On Semiconductor C5N 0.5 μm CMOS N-well process. A more detailed description of the used MAGFET can be found in Zhang, B. W., Korman, C. E. & Zaghloul, M. E., *Circular MAGFET design and SNR optimization for magnetic bead detection*, IEEE Trans. Magn. 48, (2012), which is hereby incorporated by reference. Magnetite $Fe_3O_4$ nanoparticle solutions in water with different concentrations (121 μg/mL and 1.21 mg/mL) were inject (under 2 Psi pressure) into the microfluidic channel above a MAGFET detector on the CMOS chip. A Helmholtz coil was used to generate a 60 Gauss polarization magnetic field applied on the MAGFET and the magnetic nanoparticles. The CMOS MAGFET readout circuit is shown in FIG. 8(a). The measured MAGFET output signals are shown in FIG. 8(b). When a 121 μg/mL magnetic nanoparticle solution is flowed across the CMOS sensor area, the output signal increased by about 1 dBV. This is, to our knowledge, the first experimental demonstration of a fully integrated CMOS/microfluidic hybrid microsystem without performing any wire bonding or post-processing on the CMOS die. The suitable ranges of the device dimensions are: microfluidic channels: width 200 nm to 5 mm, height: 200 nm to 5 mm; CMOS die: 1 $mm^2$ to 25 $cm^2$; contact pads: 20 μm to 200 μm per side.

It is noted that the preferred embodiment uses CMOS technology. However, the packaging method and device can be implemented with all solid state integrated circuits. And, while the invention is discussed to provide a biosensor, it can be utilized for other integrated circuits, such as microprocessors, transducers, optoelectronic devices, RF circuits, MEMS, displays, and the like. The liquid metal can be used to fabricate an on-chip antenna for wireless communication. For example, we can design the dimensions and shapes of the liquid metal filled microfluidic channel to be those of a dipole antenna operated near 2.4 GHz for Bluetooth, WiFi or other wireless communication protocols. In addition, one or more of the ICs can be a Bluetooth/wireless module utilizing the liquid metal antenna.

The preferred polymer described above is PDMS. However, any suitable polymer can be utilized, such as a curable, flexible polymer like a polyimide, polyurethane, fluorinated silicone elastomers etc. The polymer can have an embedded fiber optic channel, and the waveguides could be made of a different polymer or PDMS to provide sufficient refractive index contrast. Such fiber optic channel and waveguides can function as chip-to-chip optical interconnects to provide faster data transmission rate than pure electrical interconnects.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A non-rigid package, comprising:
   a first non-rigid polymer layer having a surface;
   an integrated circuit having an active side and a plurality of contact pads, the integrated circuit embedded in the first polymer layer, whereby the surface of the first polymer layer and the active side of the integrated circuit form a first upper surface at which the active side of the integrated circuit is flush with the surface of the polymer layer;
   a second non-rigid polymer layer having a second surface with a plurality of non-rigid microfluidic channels formed in the second surface of the second polymer layer, the second polymer layer coupled with the first polymer layer with the plurality of contact pads of said integrated circuit aligned with the plurality of microfluidic channels, wherein said first and second polymer layers fully enclose said integrated circuit; and a fluidic non-rigid conductive element received in the plurality of microfluidic channels to form an electrically conductive communication with the plurality of contact pads, wherein the conductive element is non-rigid at room temperature.

2. The package of claim 1, wherein the first surface of the first polymer layer and the integrated circuit mates with the second surface of the second polymer layer.

3. The package of claim 1, wherein the first and second polymer layer fully enclose the integrated circuit.

4. The package of claim 1, wherein the non-rigid conductive element comprises a room temperature liquid metal.

5. The package of claim 1, wherein said first and second polymer layers each comprise an elastomer such as polydimethylsiloxane (PDMS).

6. The package of claim 1, wherein the integrated circuit comprises a Complementary Metal-Oxide-Semiconductor (CMOS).

7. The package of claim 1, further comprising a sample microfluidic channel formed in the first and/or second polymer layer, said sample microfluidic channel aligned with predefined areas on the active side of the integrated circuit and configured to receive a liquid test sample and deliver the liquid test sample to the predefined areas on the integrated circuit.

8. The package of claim 1, wherein said package comprises one or a combination of a biosensor, antenna, microprocessor, or transducer.

9. The package of claim 1, wherein the package can be conformally attached by bending to a nonflat surface, and can be stretched by up to 200%.

10. A method for forming a non-rigid package, the method comprising:
providing a first non-rigid polymer layer;
embedding an integrated circuit having an active side and a plurality of contact pads in the first polymer layer, whereby the first polymer layer and the active side of the integrated circuit form a first surface;
providing a second non-rigid polymer layer having a second surface;
forming a plurality of non-rigid microfluidic channels in the second surface of the second polymer layer;
bonding the second polymer layer with the first polymer layer so that the plurality of contact pads of the integrated circuit are aligned with the plurality of microfluidic channels, whereby the first and second polymer layers fully enclose the integrated circuit; and
filling the plurality of microfluidic channels with a conductive element that is non-rigid at room temperature to form an electrically conductive communication with the plurality of contact pads.

11. The method of claim 10, wherein the channels are completely embedded in the first and second polymer layers.

12. A non-rigid micro-fluidic sensor comprising:
a first non-rigid polydimethylsiloxane (PDMS) layer;
a Complementary Metal-Oxide-Semiconductor (CMOS) die having at least one contact pad, the CMOS die embedded in the first PDMS layer;
a second non-rigid PDMS layer having at least one non-rigid microfluidic channel formed in the second PDMS layer, the second PDMS layer coupled with the first PDMS layer with the at least one contact pad of the CMOS die aligned with the at least one microfluidic channel, whereby the first and second PDMS layers fully enclose said CMOS die; and a conductive element that is non-rigid at room temperature, wherein said conductive element is received in the at least one microfluidic channels to form an electrically conductive communication with the at least one contact pad.

13. The sensor of claim 12, further comprising a sample microfluidic channel formed in the first and/or second PDMS layer, said sample microfluidic channel aligned with predefined areas on an active side of the CMOS die and configured to receive a liquid test sample and deliver the liquid test sample to the predefined areas on the CMOS die.

14. The package of claim 1, wherein at least one of the plurality of microfluidic channels has a first channel segment with a distal end connected with a lead and a proximal end connected to a respective one of the plurality of contact pads, and a second channel segment with a distal end and a proximal end connected to the respective one of the plurality of contact pads.

15. The package of claim 14, wherein the distal end of said first channel segment is in communication with an inlet port to receive the conductive element, wherein the conductive element enters the first channel segment, contacts the contact pad and enters the second channel segment.

16. The package of claim 15, wherein the distal end of said second channel segment is in communication with an outlet port to vent air.

17. The package of claim 1, wherein said first polymer layer and said second polymer layer are stretchable.

18. The package of claim 17, wherein said plurality of microfluidic channels are stretchable to form stretched microfluidic channels, and wherein said fluidic conductive element is received in the stretched microfluidic channels and maintains the electrically conductive communication with the plurality of contact pads.

19. The package of claim 17, wherein said sample microfluidic channel is stretchable to form a stretched sample microfluidic channel, and wherein the stretched sample microfluidic channel receives the liquid test sample and delivers the liquid test sample to the predefined areas on the integrated circuit.

20. The package of claim 1, wherein the integrated circuit comprises a MEMS device.

21. The package of claim 1, wherein the active side of the integrated circuit is flush with a top of the first polymer layer at the first surface.

22. The package of claim 1, said integrated circuit further having a substrate on a side opposite the active side.

23. The package of claim 1, said package having no more than two layers including the first polymer layer and the second polymer layer.

24. The package of claim 1, wherein the non-rigid conductive element comprises Indium low melting point solder or metal nanoparticle doped non-rigid materials.

25. The package of claim 24, wherein the metal nanoparticle doped non-rigid materials comprise PDMS.

* * * * *